(12) United States Patent
Brady et al.

(10) Patent No.: US 10,352,886 B2
(45) Date of Patent: Jul. 16, 2019

(54) PROBE FOR DETECTING STRUCTURAL INTEGRITY OF PART

(71) Applicant: The Boeing Company, Chicago, IL (US)

(72) Inventors: Steven K. Brady, Renton, WA (US); Landon K. Henson, Snoqualmie, WA (US); Benjamin E. Koltenbah, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 78 days.

(21) Appl. No.: 15/465,052

(22) Filed: Mar. 21, 2017

(65) Prior Publication Data

US 2018/0275081 A1 Sep. 27, 2018

(51) Int. Cl.
*G01N 27/02* (2006.01)
*G01N 27/20* (2006.01)

(52) U.S. Cl.
CPC ........... *G01N 27/025* (2013.01); *G01N 27/20* (2013.01)

(58) Field of Classification Search
CPC .................................................. G01N 27/025
USPC ......................................................... 324/654
See application file for complete search history.

(56) References Cited

U.S. PATENT DOCUMENTS

| 8,841,904 | B1 | 9/2014 | Brady et al. | |
|---|---|---|---|---|
| 2002/0130659 | A1* | 9/2002 | Wincheski | G01N 27/9033 324/235 |
| 2014/0097835 | A1* | 4/2014 | Sartee | G01R 33/07 324/251 |

* cited by examiner

*Primary Examiner* — Reena Aurora
(74) *Attorney, Agent, or Firm* — Kunzler Bean & Adamson

(57) ABSTRACT

Disclosed herein is a probe for detecting structural integrity of a part. The probe comprises an outer shield, having a hollow tubular shape, defining a first interior channel, and comprising a part-engagement end. The probe also comprises an inner shield, within the first interior channel, having a hollow tubular shape, spaced apart from the outer shield, and comprising a first end portion and a second end portion, opposite the first end portion. The first end portion of the inner shield is closer to the part-engagement end of the outer shield than the second end portion of the inner shield. The first end portion of the inner shield comprises a wall extension, protruding in a direction extending from the second end portion of the inner shield to the first end portion of the inner shield and circumferentially extending about less than an entire circumference of the inner shield.

19 Claims, 10 Drawing Sheets

PROBE FOR DETECTING STRUCTURAL INTEGRITY OF PART

FIELD

This disclosure relates generally to probes, and more particularly to probes for non-destructively detecting structural integrity of parts via electromagnetic induction.

BACKGROUND

Some conventional probes use electromagnetic induction to non-destructively inspect a metallic part for anomalies. Conventional probes use induction coils to generate and direct magnetic fields into the metallic part. The magnetic fields cause eddy currents to form in the metallic part, which induces a return magnetic field out of the part. The return magnetic field is detected by the probe and analyzed to determine whether anomalies are present in the part.

Inspection of thicker metallic parts uses magnetic fields at a lower frequency. However, magnetic fields at lower frequencies tend to decrease the signal-to-noise ratio of the probe, which reduces the sensitivity and accuracy of the probe.

SUMMARY

The subject matter of the present disclosure has been developed in response to the present state of the art, and in particular, in response to the limitations of conventional non-destructive inspection probes that rely on electromagnetic induction. Accordingly, the subject matter of the present disclosure has been developed to provide a probe for detecting structural integrity of a part that overcome at least some of the above-discussed shortcomings of relevant art techniques.

Disclosed herein is a probe for detecting structural integrity of a part. The probe comprises an outer shield, having a hollow tubular shape, defining a first interior channel, and comprising a part-engagement end. The probe also comprises an inner shield, within the first interior channel, having a hollow tubular shape, spaced apart from the outer shield, and comprising a first end portion and a second end portion, opposite the first end portion. The first end portion of the inner shield is closer to the part-engagement end of the outer shield than the second end portion of the inner shield. The first end portion of the inner shield comprises a wall extension, protruding in a direction extending from the second end portion of the inner shield to the first end portion of the inner shield and circumferentially extending about less than an entire circumference of the inner shield. The probe additionally includes an induction coil, within the first interior channel of the outer shield between the outer shield and the inner shield. The preceding subject matter of this paragraph characterizes example 1 of the present disclosure.

The probe further comprises an insulation ring, within the first interior channel between the outer shield and the inner shield and between the induction coil and the part-engagement end of the outer shield. The preceding subject matter of this paragraph characterizes example 2 of the present disclosure, wherein example 2 also includes the subject matter according to example 1, above.

The outer shield is made of a magnetic material. The inner shield is made of a magnetic material. The insulation ring is made of a non-magnetic material. The preceding subject matter of this paragraph characterizes example 3 of the present disclosure, wherein example 3 also includes the subject matter according to example 2, above.

The wall extension circumferentially extends about less than or equal to 60% of the entire circumference of the inner shield. The preceding subject matter of this paragraph characterizes example 4 of the present disclosure, wherein example 4 also includes the subject matter according to any one of examples 1-3, above.

The probe further comprises a visual indicator, external to the outer shield and radially aligned with the wall extension. The preceding subject matter of this paragraph characterizes example 5 of the present disclosure, wherein example 5 also includes the subject matter according to any one of examples 1-4, above.

The wall extension comprises a first distal end. The first distal end terminates at a first plane between the part-engagement end of the outer shield and the induction coil. The preceding subject matter of this paragraph characterizes example 6 of the present disclosure, wherein example 6 also includes the subject matter according to any one of examples 1-5, above.

The first end portion of the inner shield further comprises a cut-out space contiguous with the wall extension and extending about less than entire circumference of the inner shield. The preceding subject matter of this paragraph characterizes example 7 of the present disclosure, wherein example 7 also includes the subject matter according to any one of examples 1-6, above.

The probe further comprises a magnetic field sensor positioned at each of multiple locations within the cut-out space of the inner shield. The preceding subject matter of this paragraph characterizes example 8 of the present disclosure, wherein example 8 also includes the subject matter according to example 7, above.

Also disclosed herein is a probe for detecting structural integrity of a part. The probe comprises an outer shield, having a hollow tubular shape, defining a first interior channel, and comprising a part-engagement end. The probe also comprises an inner shield, within the first interior channel, having a hollow tubular shape, spaced apart from the outer shield, and comprising a first proximal end and a first distal end, opposite the first proximal end. The probe further comprises an induction coil, within the first interior channel of the outer shield between the outer shield and the inner shield. The first distal end of the inner shield terminates at a first plane between the part-engagement end of the outer shield and the induction coil. The preceding subject matter of this paragraph characterizes example 9 of the present disclosure.

The first distal end of the inner shield has an at least partially annular shape. The preceding subject matter of this paragraph characterizes example 10 of the present disclosure, wherein example 10 also includes the subject matter according to example 9, above.

The first plane is a first distance away from the part-engagement end of the outer shield. The induction coil is a third distance away from the part-engagement end of the outer shield. The first distance is at most about half of the third distance. The preceding subject matter of this paragraph characterizes example 11 of the present disclosure, wherein example 11 also includes the subject matter according to any one of examples 9 or 10, above.

The inner shield further comprises a first end portion and a second end portion, opposite the first end portion. The first end portion of the inner shield comprises a wall extension, protruding in a direction extending from the second end portion of the inner shield to the first end portion of the inner shield and circumferentially extending about less than an entire circumference of the inner shield. The first distal end of the inner shield is defined by the wall extension. The preceding subject matter of this paragraph characterizes example 12 of the present disclosure, wherein example 12 also includes the subject matter according to any one of examples 9-11, above.

The first plane is a first distance away from the part-engagement end of the outer shield. The first end portion of the inner shield further comprises a cut-out space contiguous with the wall extension and extending about less than entire circumference of the inner shield. The first end portion of the inner shield further comprises a second distal end of the inner shield. The wall extension and the second distal end of the inner shield define the cut-out space. The second distal end of the inner shield terminates at a second plane. The second plane is a second distance away from the part-engagement end of the outer shield. The second distance is greater than the first distance. The preceding subject matter of this paragraph characterizes example 13 of the present disclosure, wherein example 13 also includes the subject matter according to example 12, above.

The probe further comprises a magnetic field sensor positioned at each of multiple locations within the first interior channel of the outer shield. Each magnetic field sensor is positioned at least a fourth distance away from the part-engagement end of the outer shield and at most a fifth distance away from the part-engagement end of the outer shield. The preceding subject matter of this paragraph characterizes example 14 of the present disclosure, wherein example 14 also includes the subject matter according to example 13, above.

Additionally disclosed herein is a probe for detecting structural integrity of a part. The probe comprises an outer shield, having a hollow tubular shape, defining a first interior channel, and comprising a part-engagement end. The probe also comprises an inner shield, within the first interior channel, having a hollow tubular shape, spaced apart from the outer shield. The probe further comprises an induction coil, within the first interior channel of the outer shield between the outer shield and the inner shield. The probe additionally comprises at least one sensor assembly within the first interior channel of the outer shield between the part-engagement end of the outer shield and the induction coil. The at least one sensor assembly comprises at least two magnetic field sensors stacked together. The preceding subject matter of this paragraph characterizes example 15 of the present disclosure.

The probe further comprises an insulation ring within the first interior channel between the outer shield and the inner shield. The at least one sensor assembly is coupled directly to the insulation ring. The preceding subject matter of this paragraph characterizes example 16 of the present disclosure, wherein example 16 also includes the subject matter according to example 15, above.

The inner shield comprises a distal end. The insulation ring suspends the at least one sensor assembly in an axially spaced apart manner relative to the distal end of the inner shield and the part-engagement end of the outer shield. The preceding subject matter of this paragraph characterizes example 17 of the present disclosure, wherein example 17 also includes the subject matter according to example 16, above.

The at least two magnetic field sensors of the at least one sensor assembly are stacked together in a direction perpendicular to a central axis of the outer shield and the inner shield. The preceding subject matter of this paragraph characterizes example 18 of the present disclosure, wherein example 18 also includes the subject matter according to any one of examples 15-17, above.

The probe comprises multiple sensor assemblies spaced apart from each other about at least a portion of a circumference of the inner shield. The preceding subject matter of this paragraph characterizes example 19 of the present disclosure, wherein example 19 also includes the subject matter according to any one of examples 15-18, above.

The inner shield comprises a first end portion and a second end portion, opposite the first end portion. The first end portion of the inner shield is closer to the part-engagement end of the outer shield than the second end portion of the inner shield. The first end portion of the inner shield comprises a wall extension, protruding in a direction extending from the second end portion of the inner shield to the first end portion of the inner shield and circumferentially extending about less than an entire circumference of the inner shield. The wall extension defines a distal end of the inner shield that terminates at a first plane between the part-engagement end of the outer shield and the induction coil. The first end portion of the inner shield further comprises a cut-out space contiguous with the wall extension and extending about less than entire circumference of the inner shield. The at least one sensor assembly is at least partially within the cut-out space of the first end portion of the inner shield. The preceding subject matter of this paragraph characterizes example 20 of the present disclosure, wherein example 20 also includes the subject matter according to any one of examples 15-19, above.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

DETAILED DESCRIPTION

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

The probe of the present disclosure facilitates the use of low-frequency magnetic fields to accurately detect small cracks in relatively thick metallic parts by focusing the magnetic flux of the magnetic fields into the part. By focusing the magnetic flux into the part, a resultant signal-to-noise ratio of the probe is increased, which improves the sensitivity and accuracy of the probe. The structure of the probe configured to focus the magnetic flux of the magnetic fields also promotes the identification of the directionality of deformations in the parts inspected by the probe. Additionally, the signal-to-noise ratio and the sensitivity of the probe is increased by utilizing sensor assemblies with stacked and redundant magnetic field sensors.

Figure 1:
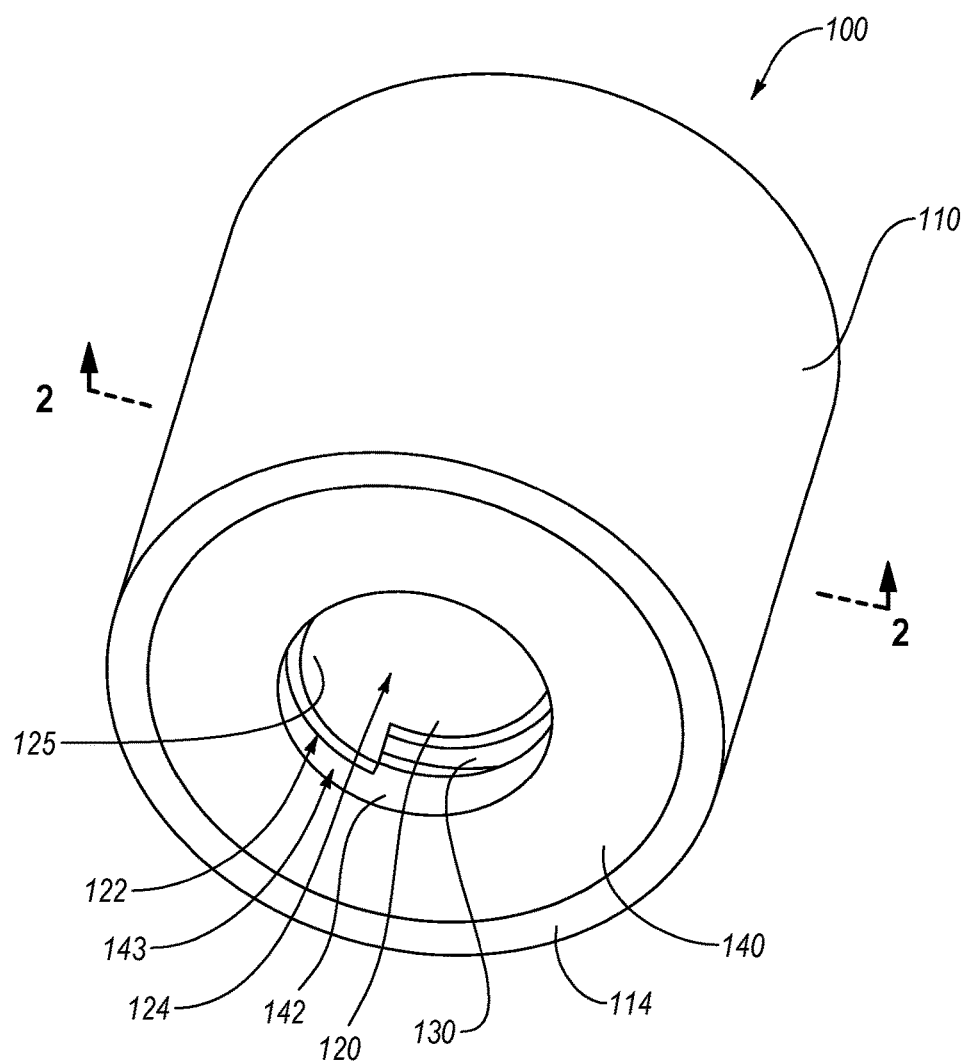
FIG. 1 is a schematic perspective view of a probe, according to one or more examples of the present disclosure.
Figure 2:
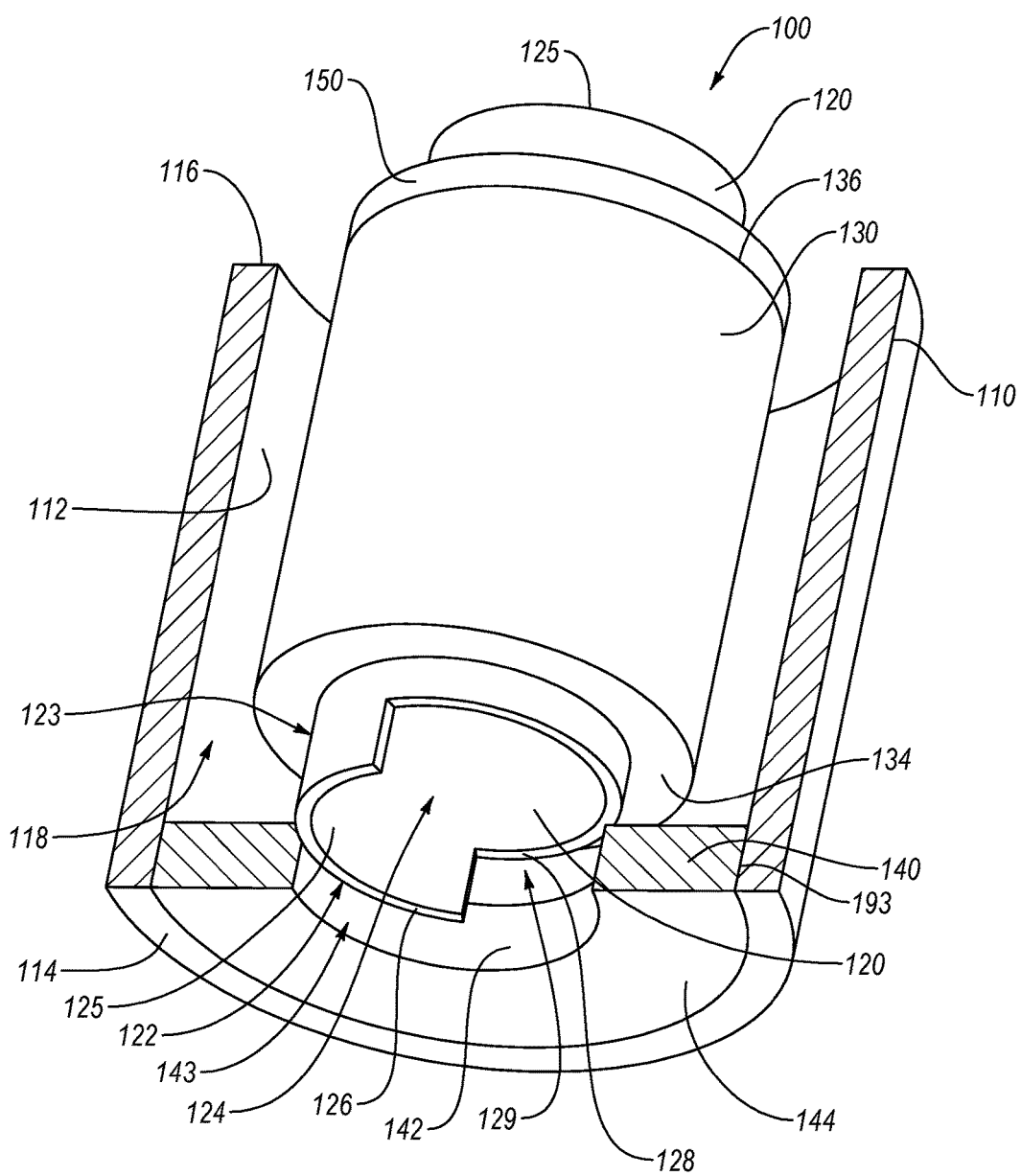
FIG. 2 is a schematic, partial cross-sectional, perspective view of the probe of FIG. 1, taken along the line 2-2 of FIG. 1, according to one or more examples of the present disclosure.

Referring to FIGS. 1 and 2, one embodiment of a probe 100 for detecting structural integrity of a part is shown. The structural integrity of a part is dependent on structural anomalies, such as cracks or stresses, in the part. Accordingly, in one implementation, the probe 100 detects structural anomalies, such as cracks, in the part.

Figure 5:
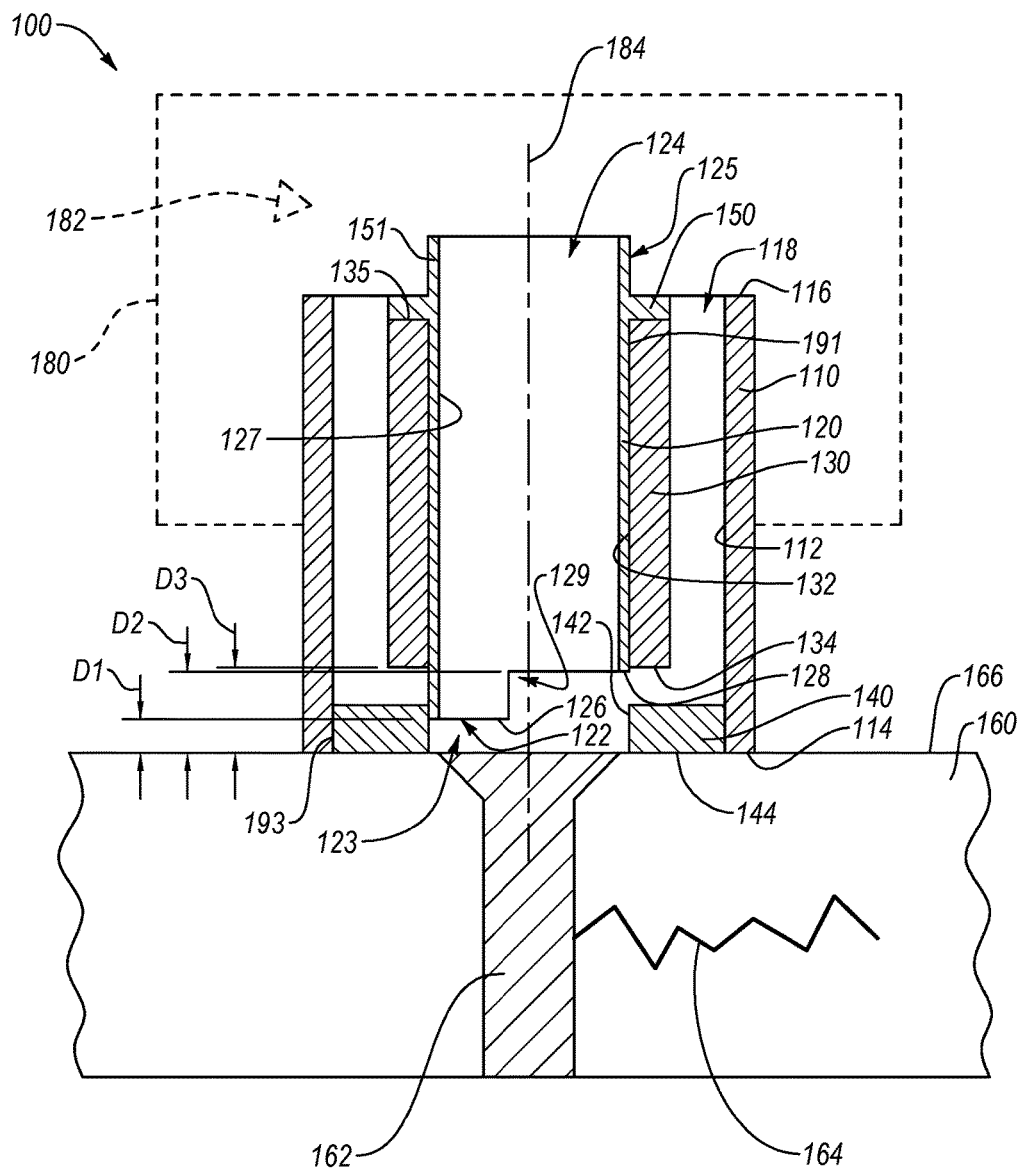
FIG. 5 is a schematic cross-sectional side elevation view of the probe of FIG. 1, taken along the line 2-2 of FIG. 1 and shown engaged with a part, according to one or more examples of the present disclosure.

The probe 100 includes an outer shield 110. Generally, as shown in FIG. 2, the outer shield 110 has a hollow tubular shape. Therefore, the outer shield 110 is elongate and includes an interior surface 112 that defines a first interior channel 118 extending lengthwise from a part-engagement end 114 of the outer shield 110 to a proximal end 116 of the outer shield 110. The hollow tubular shape of the outer shield 110 can have any of various cross-sectional shapes, such as circular as shown. The proximal end 116 is opposite the part-engagement end 114. Furthermore, the part-engagement end 114 is configured to engage a part during an inspection of the part by the probe 100. As shown in FIG. 5, according to one example, engagement between a part 160 and the part-engagement end 114 includes flush mounting the part-engagement end 114 directly against the part 160. The part-engagement end 114 is a flat, annular-shaped surface that is perpendicular to a central axis 184 of the probe 100 in one example. The central axis 184 of the probe is co-axial with a central axis of the outer shield 110. The outer shield 110 is made of a magnetic material, such as iron or other ferromagnetic or ferrimagnetic materials.

Figure 4:
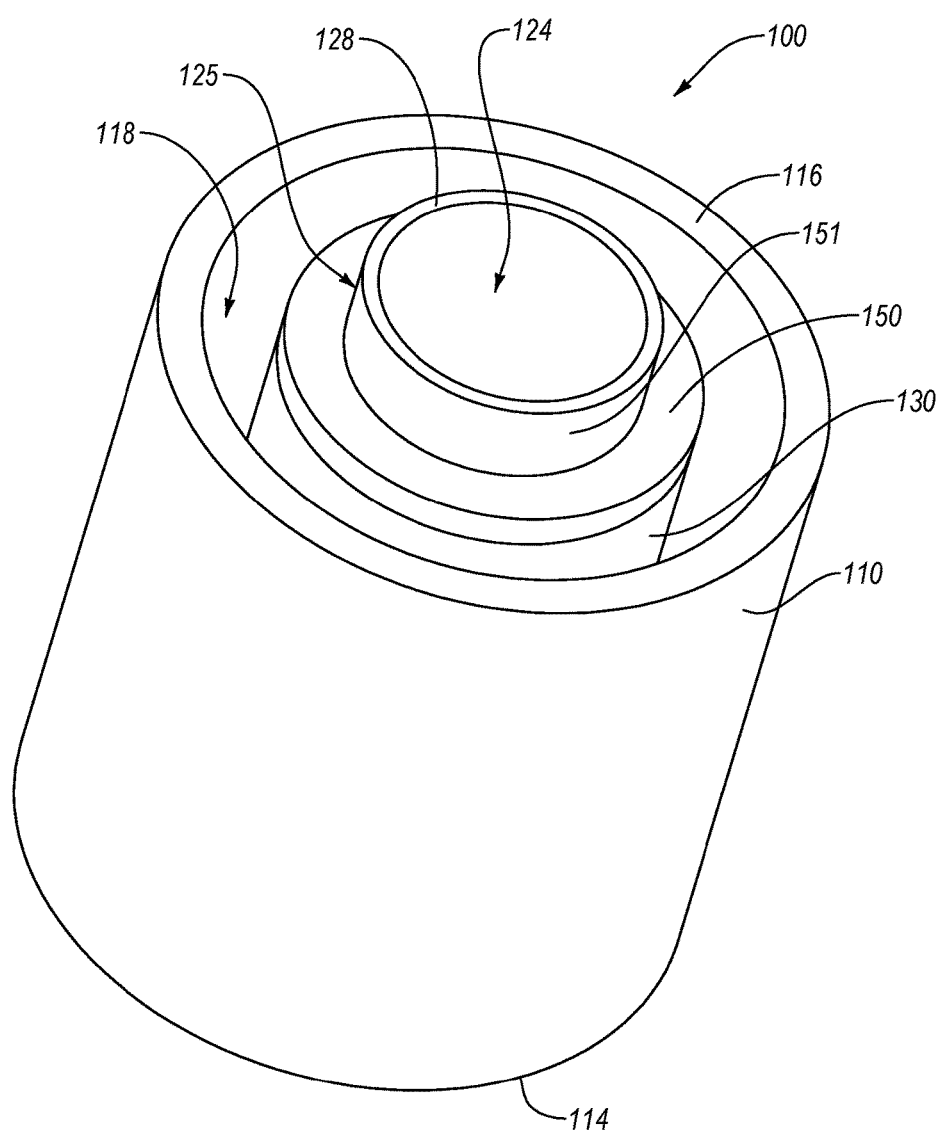
FIG. 4 is a schematic perspective view of the probe of FIG. 1, according to one or more examples of the present disclosure.

The probe 100 also includes an inner shield 120. Generally, the inner shield 120 has a hollow tubular shape. Therefore, the inner shield 120 is elongate and includes an interior surface 127 that define a second interior channel 124 extending lengthwise from a first end portion 123 to a second end portion 125. The inner shield 120 also includes an exterior surface 191 opposite the interior surface 127. The hollow tubular shape of the inner shield 120 can have any of various cross-sectional shapes, such as circular as shown. The first end portion 123 of the inner shield 120 is opposite the second end portion 125 of the inner shield 120. Furthermore, the first end portion 123 of the inner shield 120 is closer to the part-engagement end 114 of the outer shield 110 than the second end portion 125 of the inner shield 120. In other words, the first end portion 123 is located proximate the part-engagement end 114 of the outer shield 110 and the second end portion 125 is located proximate the proximal end 116 of the outer shield 110. The inner shield 120 is within the first interior channel 118 of the outer shield 110. More specifically, in one implementation shown in FIGS. 4 and 5, an entirety of the inner shield 120, except a neck 151 of the second portion 125, is located within the first interior channel 118 of the outer shield 110. Moreover, the inner shield 120 is positioned and oriented within the first interior channel 118 such that a central axis of the inner shield 120 is co-axial with the central axis 184 of the probe 100. Accordingly, the central axes of the outer shield 110 and the inner shield 120 are co-axial with each other and the central axis 184 of the probe 100. For this reason, the central axis 184 may also represent the central axes of the outer shield 110 and the inner shield 120. The inner shield 120 is made of a magnetic material, such as iron or other ferromagnetic or ferrimagnetic materials.

Figure 6:
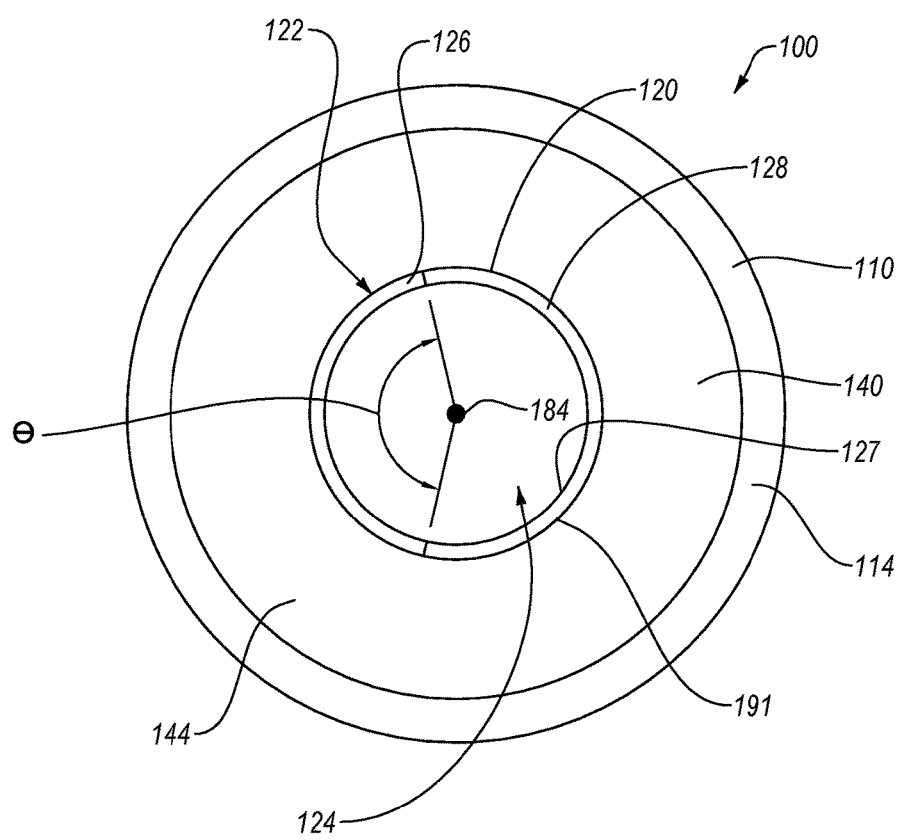
FIG. 6 is a schematic bottom plan view of the probe of FIG. 1, according to one or more examples of the present disclosure.

The first end portion 123 of the inner shield 120 includes a wall extension 122. The wall extension 122 protrudes in a direction extending from the second end portion 125 of the inner shield 120 to the first end portion 123 of the inner shield 120. The hollow tubular shape of the inner shield 120 is defined by a circumferentially closed elongate wall that is continuous about a 360-degree circumference (e.g., perimeter) of the inner shield 120. It is noted that the wall of the inner shield 120 may have a non-circular cross-sectional shape (e.g., ovular, triangular, square, etc.) and still be continuous about a 360-degree circumference of the inner shield 120. At the first end portion 123 of the inner shield 120, only part or a section (e.g., the wall extension 122) of the circumferentially closed elongate wall extends or protrudes away from the remaining circumferentially closed elongate wall to form a tab-like structure. Accordingly, the wall extension 122 circumferentially extends about less than an entire circumference of the inner shield 120. Referring to FIG. 6, the wall extension 122 extends about an angle θ of the entire 360-degree circumference of the inner shield 120. The angle θ is more than 0-degees, but less than 360-degrees such that the first distal end 126 of the inner shield 120 has an at least partially annular shape. In one implementation, the angle θ is equal to or less than 180-degrees, which for a circular inner shield 120 (e.g., with an annular elongate wall) is equal to or less than 50% of the entire circumference of the inner shield 120. According to other implementations, the angle θ is between about 120-degrees and about 210-degrees, which for a circular inner shield 120 is between about 30% and about 60% of the entire circumference of the inner shield 120. As illustrated, for a circular inner shield 120, the wall extension 122 has a generally arcuate shape. For example, in one implementation, the angle θ is 180-degrees and the wall extension 122 has a generally semi-circular shape.

Because the wall extension 122 extends about less than an entire circumference of the inner shield 120, the wall extension 122 partially defines a cut-out space 129. The cut-out space 129 is contiguous with the wall extension 122 and extends about less than an entire circumference of the inner shield 120. The wall extension 122 and the cut-out space 129 collectively extend about the entire circumference of the inner shield 120. The cut-out space 129, as well as the wall extension 122, can be formed by cutting out a portion of the inner shield 120 after the inner shield 120 is formed in one example. In another example, the cut-out space 129 is co-formed with the inner shield 120, such as in a casting or co-molding process. The wall extension 122 defines a first distal end 126 of the inner shield 120. Defining the cut-out space 129 is a second distal end 128 of the inner shield 120. While the first distal end 126 and the second distal end 128 are parallel to each other in some implementations, the first distal end 126 and the second distal end 128 are not co-planar in other implementations. In other words, the first distal end 126 is axially spaced apart (e.g., spaced apart in a direction parallel to the central axis 184) from the second distal end 128. Accordingly, the first distal end 126 can be considered a distalmost end of the inner shield 120.

The second end portion 125 of the inner shield 120 includes a shoulder 150 and the neck 151. The shoulder 150 protrudes radially outwardly from the exterior surface 191 of the inner shield 120. In some implementations, the inner shield 120 is positioned within the interior channel 118 of the outer shield 110 such that the shoulder 150 is flush with the proximal end 116 of the outer shield 110. The neck 151 protrudes from the shoulder 150 along the central axis 184.

The probe 100 further includes an induction coil 130. The induction coil 130 is entirely within the first interior channel 118 of the outer shield 110 and between the outer shield 110 and the inner shield 120. Moreover, the induction coil 130 is wound around the inner shield 120 such that the induction coil 130 is between the outer shield 110 and the inner shield 120. In one implementation, the induction coil 130 is placed on or wound onto the exterior surface 191 of the inner shield 120. The induction coil 130 includes a wire (e.g., an enameled magnet wire) that is wound around the inner shield 120 to form a solenoid. The turns of the induction coil 130 generate a magnetic field when an AC current flows through the induction coil 130. The magnitude and frequency of the magnetic field is adjustable by adjusting the power and frequency of the AC current. The outer shield 110 and the inner shield 120, being made of a magnetic material, help to centralize the magnetic field and limit the exposure of the magnetic field to areas external to the outer shield 110 by attracting the magnetic field. In one implementation, the shoulder 150 provides a stop against which the induction coil 130 abuts.

The induction coil 130 is elongate and extends in a lengthwise direction from a distal end 134 to a proximal end 135. The proximal end 135 is opposite the distal end 134. Generally, the distal end 134 is the distalmost end of the induction coil 130. In some implementations, the induction coil 130 may also include upper and lower end caps that cover upper and lower portions of the solenoid. In such implementations, the upper and lower end caps define the proximal end 135 and the distal end 134 of the induction coil 130. Accordingly, although shown as one piece in the figures, the induction coil 130 may include multiple pieces (e.g., wires, caps, etc.). Nevertheless, whether one piece or multiple pieces, all pieces of the induction coil are considered to form the representation of the induction coil 130 in the figures.

The probe 100 additionally includes an insulation ring 140. The insulation ring 140 is within the first interior channel 118 of the outer shield 110. More specifically, the insulation ring 140 is between the outer shield 110 and the inner shield 120 in a radial direction (e.g., perpendicular to the central axis 184) and between the induction coil 130 and the part-engagement end 114 of the outer shield 110 in an axial direction (e.g., parallel to the central axis 184). The insulation ring 140 has a generally annular shape and includes an interior surface 142 that defines a third interior channel 143. The third interior channel 143 is sized to be equal to or larger than the size of the exterior surface 191 of the inner shield 120. Accordingly, the second interior channel 124 and the third interior channel 143 are continuous and collectively define a through channel of the probe 100. In some implementations, the interior surface 142 abuts the exterior surface 191 of the wall extension 122. An exterior surface 193 of the insulation ring 140 abuts the interior surface 112 of the outer shield 110. Moreover, insulation ring 140 is positioned and oriented within the first interior channel 118 such that a central axis of the insulation ring 140 is co-axial with the central axis 184 of the probe 100. Accordingly, the central axes of the outer shield 110, the inner shield 120, and the insulation ring 140 are co-axial with each other and the central axis 184 of the probe 100. For this reason, the central axis 184 may also represent the central axis of the insulation ring 140. The insulation ring 140 is made of a non-magnetic material, such as a polymer (e.g., plastic, rubber, epoxy, resin, etc.). The insulation ring 140 is pre-formed and attached (e.g., bonded) to the interior surface 112 of the outer shield 110 in one implementation. In another implementation, the insulation ring 140 is formed in place within the interior surface 112 of the outer shield 110.

The insulation ring 140 is proximate the part-engagement end 114 of the outer shield 110 and the first end portion 123 of the inner shield 120. In one implementation, the insulation ring 140 has a distal surface 144 that is flat and flush (e.g., co-planar) with the part-engagement end 114 of the outer shield 110. As will be explained in more detail below, the insulation ring 140 facilitates the placement of sensor assemblies 170 within the first interior channel 118. Furthermore, in some implementations, the insulation ring 140 promotes structural stability of the inner shield 120 relative to the outer shield 110.

Referring to FIG. 5, the probe 100 is operable to detect structural integrity (e.g., crack 164) of a part 160 by positioning the probe 100 on an exterior surface 166 of the part 160 at a target location of the part 160. Cracks tend to initiate from fasteners in the part 160. Accordingly, in one implementation, the target location of the part 160 is a location of the part where a fastener 162 is present. In the illustrated implementation, the probe 100 is positioned on the exterior surface 166 of the part 160 over or about the fastener 162 in the part. However, it is recognized that the probe 100 can be positioned on the exterior surface 166 of the part 160 at any of various other locations of the part, including locations where no fastener is present. Positioning the probe 100 on the exterior surface 166 of the part 160 includes directly engaging (e.g., mounting flush) the part-engagement end 114 of the probe 100 with the exterior surface 166 of the part 160.

Figure 7:
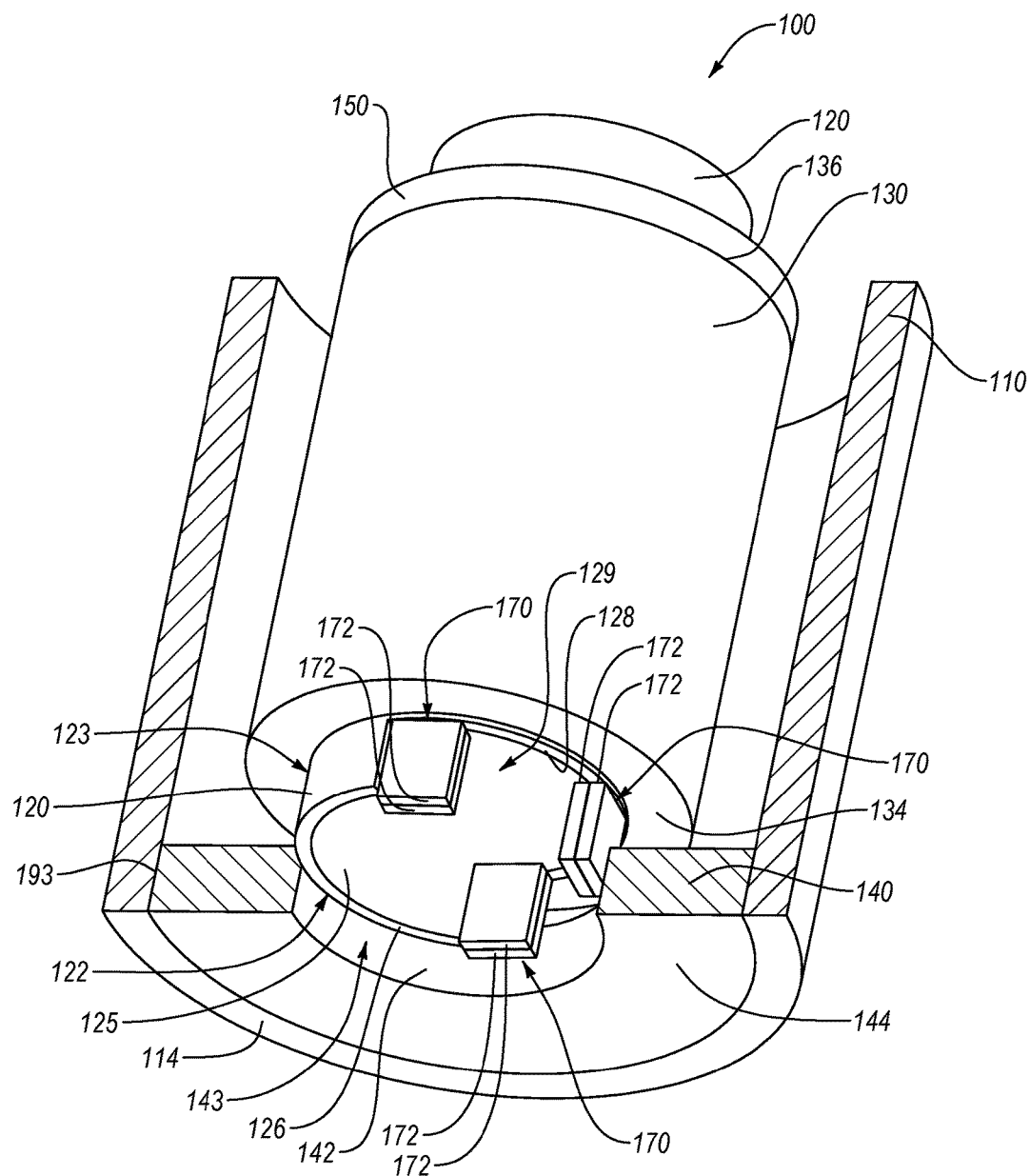
FIG. 7 is a schematic, partial cross-sectional, perspective view of a probe, according to one or more examples of the present disclosure.

With the probe 100 positioned on the exterior surface 166 of the part 160, electric current is passed through the induction coil 130 to generate a magnetic field. The direction of the flow of electric current is such that the magnetic field generated by the induction coil 130 is directed into the part 160. In response to the magnetic field, eddy currents form in the part 160. The eddy currents generate a return magnetic field, which can be detected by magnetic field sensors, such as the magnetic field sensors 172 (see, e.g., FIG. 7). The characteristics of the return magnetic field correspond with the structural integrity of the part 160. For example, the return magnetic field from a part without structural anomalies may have first characteristics and the return magnetic field from a part without structural anomalies may have second characteristics. All other things being equal, if the second characteristics are different than the first characteristics, then it can be determined that an anomaly, which changes the characteristics of the return magnetic field as the magnetic field passes through the anomaly, is present in the part. To detect relatively small anomalies in parts, the frequency of the magnetic field directed into the part should be small. However, with conventional probes, the smaller the frequency, the lower the sensitivity of the probe. To solve this problem and promote the sensitivity of the probe 100, even while using magnetic fields with small frequencies, the probe 100 utilizes the structural geometry of the wall extension 122 of the inner shield 120 and a lift-off of the inner shield 120 relative to the surface 166 of the part 160.

The wall extension 122 acts to redirect and focus the magnetic field generated by the induction coil 130 and directed into the part 160. More specifically, the wall extension 122 acts to reflect the magnetic field and contain more of the electromagnetic energy within a tighter volume than it would otherwise occupy in the absence of the wall extension 122. With the magnetic field more contained, the strength of the field penetrating the part 160 is larger, and the resulting return magnetic field in proximity of the sensors is also larger, which improves the sensor signal. By focusing the magnetic field, a more concentrated and higher-intensity magnetic field is passed into the part 160, which increases the overall signal-to-noise ratio of the probe 100 and allows the magnetic field to penetrate deeper into the part 160.

Additionally, the induction coil 130 redirects the magnetic field in a particular direction. In other words, the induction coil 130 concentrates the magnetic field in a particular direction, which introduces an element of directionality to the magnetic field. By knowing the directionality of the magnetic field, the probe 100 is able to determine a directionality or orientation of an anomaly detected by the probe 100. For example, in one implementation, the wall extension 122 concentrates the magnetic field in a direction extending radially inwardly away from the wall extension 122 and toward the central axis 184. Accordingly, when an anomaly is detected by the probe 100, the orientation of the anomaly corresponds with the orientation of the wall extension 122. More specifically, knowing the orientation of the wall extension 122 relative to the part 160, the probe 100 is able to detect the orientation of anomaly detected by the probe 100. According to one example shown in FIG. 5, the wall extension 122 is configured to focus the magnetic field generated by the induction coil 130 in a leftward-to-rightward direction on the page such that when the crack 164 is detected, the leftward-to-rightward orientation of the crack 164 is also detected. In some embodiments, the probe 100 is rotated 360-degrees about its central axis 184 when over the fastener 162. As the probe 100 rotates and an anomaly is detected, the rotational position of the probe 100 (e.g., the wall extension 122) helps identify the orientation of the anomaly. To move the probe 100 relative to the part 160 or to provide additional structure to the probe 100, the probe 100 can include a handling assembly 180 coupled to the outer shield 110 and/or the inner shield 120. The handling assembly 180 includes a body, transmission lines, end effector, robot, and/or the like in some implementations.

Figure 3:
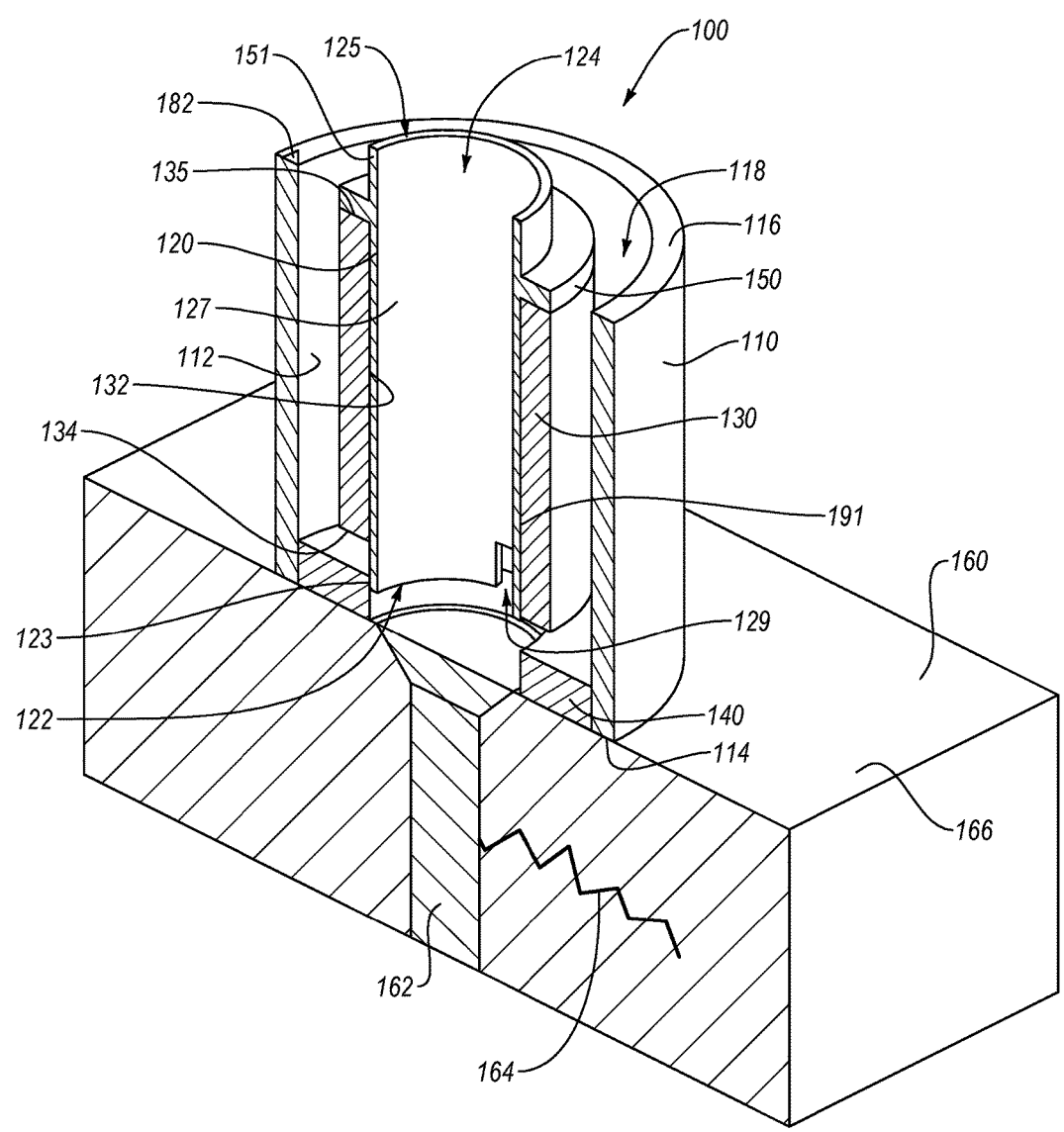
FIG. 3 is a schematic, cross-sectional, perspective view of the probe of FIG. 1, taken along the line 2-2 of FIG. 1 and shown engaged with a part, according to one or more examples of the present disclosure.

According to some implementations shown in FIGS. 3 and 5, the probe 100 includes a visual indicator 182 that is external to, and in some cased formed on, the outer shield 110. The location of the visual indicator 182 on the probe 100 corresponds with the location of the wall extension 122. For example, the visual indicator 182 is radially aligned with (e.g., positioned radially outward of) a center of the wall extension 122. In one implementation, the visual indicator 182 is an indicia formed, printed, or bonded on the probe 100. Alternatively, the visual indicator 182 is a power line (e.g., chord) that supplies power to the induction coil 130.

The lift-off of the inner shield 120 relative to the part-engagement end 114 of the outer shield 110, and thus the exterior surface 166 of the part 160 when the part-engagement end 114 is engaged with the part 160, also helps to focus the magnetic field generated by the induction coil 130 and helps increase the signal-to-noise ratio of the probe 100. The lift-off focuses the magnetic field and increases the signal-to-noise ratio of the probe 100 by help to reflect and shape (e.g., concentrate) the magnetic field. Referring to FIG. 5, the first distal end 126 of the inner shield 120 is coextensive with a first plane, perpendicular to the central axis 184, that is a first distance D1 from the part-engagement end 114 of the outer shield 110 and the second distal end 128 of the inner shield 120 is coextensive with a second plane, perpendicular to the central axis 184, that is a second distance D2 from the part-engagement end 114. Furthermore, the distal end 134 of the induction coil 130 is coextensive with a third plane, perpendicular to the central axis 184, that is a third distance D3 from the part-engagement end 114 of the outer shield 110. When the part-engagement end 114 of the outer shield 110 is engaged with the exterior surface 166 of the part 160, the first distance D1, the second distance D2, and the third distance D3 can be the respective distances from the exterior surface 166 of the part 160. The first distance D1 is greater than zero and less than the second distance D2 and the third distance D3. The first distance D1 being greater than zero and less than the third distance D3 creates a gap between the exterior surface 166 of the part 160 and the inner shield 120 and an offset (in the axial direction) between the first distal end 126 of the inner shield 120 and the distal end 134 of the induction coil 130. This gap and offset help to focus the magnetic field generated by the induction coil 130.

In some implementations, the second distance D2 is equal to the third distance D3. However, as shown, in certain implementations, the second distance D2 is less than the third distance D3. The first distance D1 is between about 30% and about 70% of the third distance D3 in some implementations. In one implementation, the first distance D1 is about 50% (or at most about 50%) of the third distance D3. Additionally, in some implementations, the first distance D1 is between about 20% and about 80% of the second distance D2. In one implementation, the first distance D1 is about 50% of the second distance D2. The distances referred to herein are axial distances or distances parallel to the central axis 184 of the probe 100.

Figure 8:
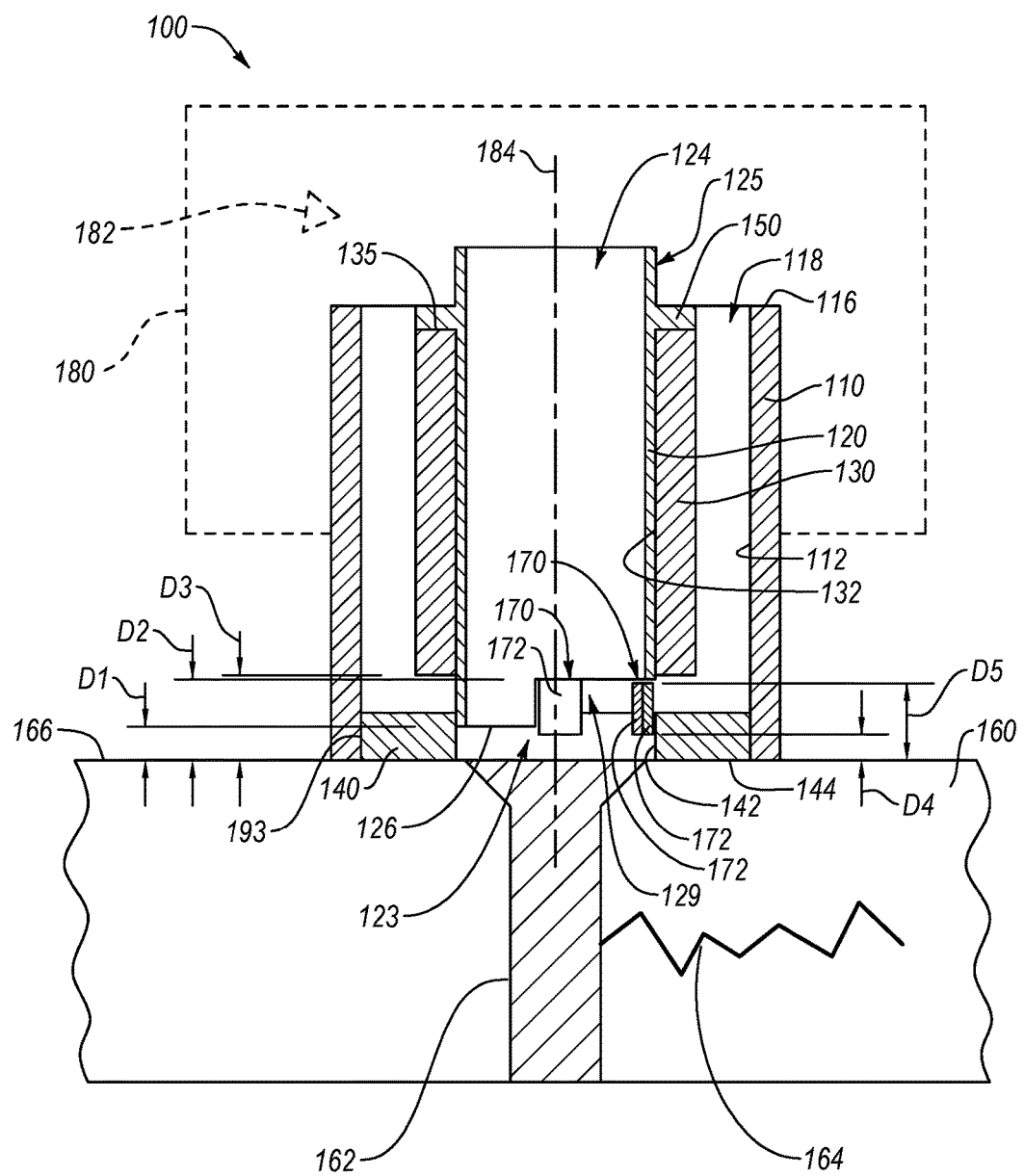
FIG. 8 is a schematic cross-sectional side elevation view of the probe of FIG. 7, according to one or more examples of the present disclosure.

Referring to FIGS. 7-10, in some embodiments, the probe 100 includes at least one sensor assembly 170 within the first interior channel 118 of the outer shield 110. In some implementations, the sensor assembly 170 is located at least partially within the cut-out space 129 of the first end portion 123 of the inner shield 120. The sensor assembly 170 includes at least two sensors 172. The sensor assembly 170 is between the part-engagement end 114 of the outer shield 110 and the induction coil 130. More specifically, as shown in FIG. 8, the sensors 172 of each sensor assembly 170 are positioned at least a fourth distance D4 away from the part-engagement end 114 and at most a fifth distance D5 away from the part-engagement end 114. When the part-engagement end 114 of the outer shield 110 is engaged with the exterior surface 166 of the part 160, the fourth distance D4 and the fifth distance D5 can be the respective distances from the exterior surface 166 of the part 160. The fourth distance D4 is greater than zero in some implementations. Moreover, the fourth distance D4 is less than the first distance D1 in certain implementations. The fifth distance D5 is less than the second distance D2 and the third distance D3 in some implementations. However, in certain implementations, the fourth distance D4 is equal to the first distance Dl.

The probe 100 includes multiple sensor assemblies 170 in some embodiments. The multiple sensor assemblies 170 are spaced apart from each other about, but not necessarily in contact with, at least a portion of the circumference of the inner shield 120. For example, in the illustrated implementation, the probe 100 includes three sensor assemblies 170 located within the cut-out space 129 and spaced an equal distance apart from each other. In one implementation, the angle θ is about 180-degrees and the multiple sensor assemblies 170 are positioned about 90-degrees apart from each other about the circumference of the inner shield 120 within the cut-out space 129. Although three sensor assemblies 170 positioned an equal distance apart from each other are shown, in other implementations, the probe 100 includes two or more than three sensors assemblies 170 spaced an equal distance or unequal distance apart from each other.

Each sensor 172 of each sensor assembly 170 is a magnetic field sensor. Each sensor 172 has at least one receptor that is sensitive to magnetic fields. For example, in the presence of a magnetic field, the at least one receptor may promote the flow of electrons at a flow rate proportional to the magnitude of the magnetic field. As another example, in the presence of a magnetic field, the at least one receptor may promote the flow of electrons in a direction corresponding with the direction of the magnetic field. The characteristics of the flow of electrons are converted into an electric signal representative of the characteristics of the flow of electrons, which are in turn representative of the characteristics of a sensed magnetic field. The electric signal (i.e., sensor signal) is then utilized by a control module integrated into the sensor 172 or external to the sensor 172 (e.g., external to the outer shield 110) and electrically coupled with the sensor 172 to determine the characteristics of the sensed magnetic field. The control module may then compare the sensed magnetic field with an expected magnetic field to determine whether anomalies are present in the part 160. The control module includes at least one of logic hardware and executable code, the executable code being stored on one or more memory devices. The executable code may be replaced with a computer processor and computer-readable storage medium that stores executable code executed by the processor. In some implementations, each sensor 172 includes a magnetometer, such as any of various magnetometers known in the art. In other implementations, each sensor 172 is a load sensor attached to a ferromagnetic or similar material that measures force. According to some implementations, each sensor 172 is a so-called giant magnetoresistive (GMR) sensor.

In certain implementations, each sensor 172 is configured to sense a magnetic field that has magnetic flux parallel to a sensitive axis of the sensor 172. Accordingly, each sensor 172 can be oriented with respect to its sensitive axis to detect only those magnetic fields that have a desired flux direction corresponding with the orientation of the sensitive axis of the sensor 172. In one implementation, the sensitive axes of the sensors 172 of a given sensor assembly 170 are aligned or parallel. However, in other implementations, the sensitive axes of the sensors 172 of a given sensor assembly 170 are misaligned or nonparallel.

The sensors 172 of each sensor assembly 170 are stacked together. In other words, the sensors 172 of a given sensor assembly 170 abut each other in a side-by-side or end-to-end manner. In some implementations, abutting sensors 172 of a sensor assembly 170 can be coupled in direct contact with each other with an adhesive, bonding agent, fastener, or other coupling technique. Accordingly, two sensors 170 are stacked together and considered to abut each other even if a thin intermediate layer, such as a bonding layer, is in direct contact with the sensors 170. A sensor assembly 170 with two or more stacked sensors 172 facilitates a more accurate detection of magnetic fields compared to a single sensor 172. In one implementation, the sensors 172 of the sensor assembly 170 each independently detect virtually the same magnetic field at virtually the same location. The separate magnetic fields detected by the sensors 172 of a given sensor assembly 170 are then compared to each other (e.g., averaged) and a single magnetic field value (e.g., an average value) is determined based on the comparison. Such a stacked configuration of sensors 172 helps to increase the sensitivity and accuracy of the probe 100.

The sensor assemblies 170 are oriented within the interior channel 118 of the outer shield 110 such that the sensors 172 of the sensor assemblies 170 are stacked in a desired stack direction or the direction in which the sensors 172 are stacked. In the illustrated implementation, the stack direction of the sensors 172 of each sensor assembly 170 is a radial direction that is perpendicular to the central axis 184 of the probe 100. However, in other implementations, the stack direction may be angled relative to the central axis 184 at an angle other than 90-degrees. Still further, in certain implementations, the stack direction may be parallel to the central axis 184. As mentioned above, the stack direction of the sensor assemblies 170 is chosen to detect a magnetic field with a desired flux direction.

Figure 9:
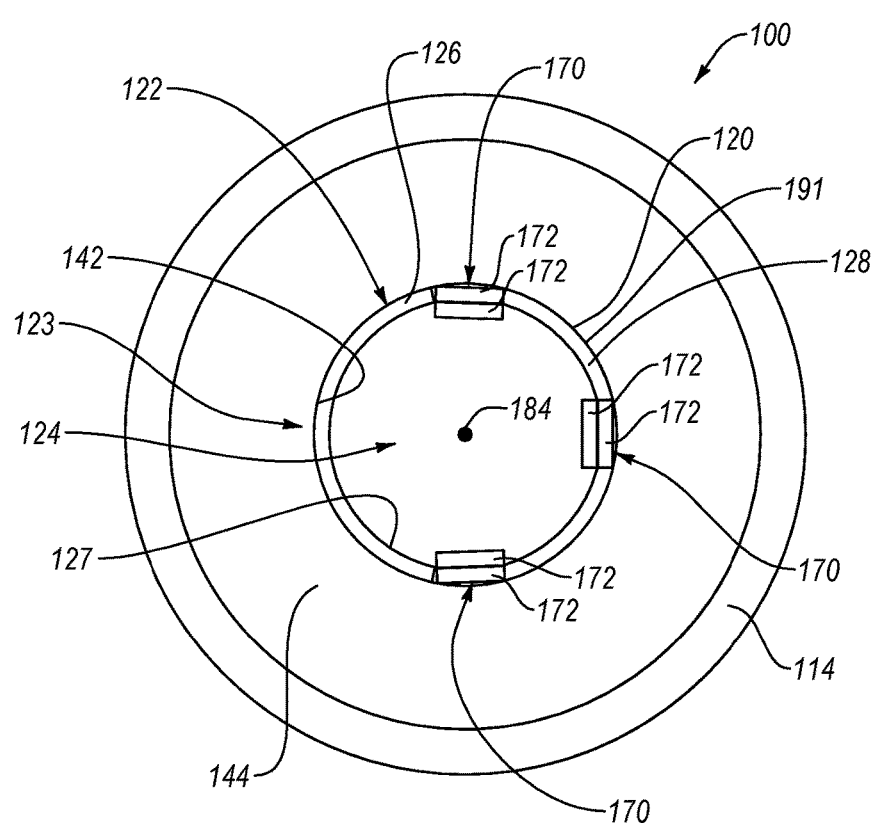
FIG. 9 is a schematic bottom plan view of the probe of FIG. 7, according to one or more examples of the present disclosure.
Figure 10:
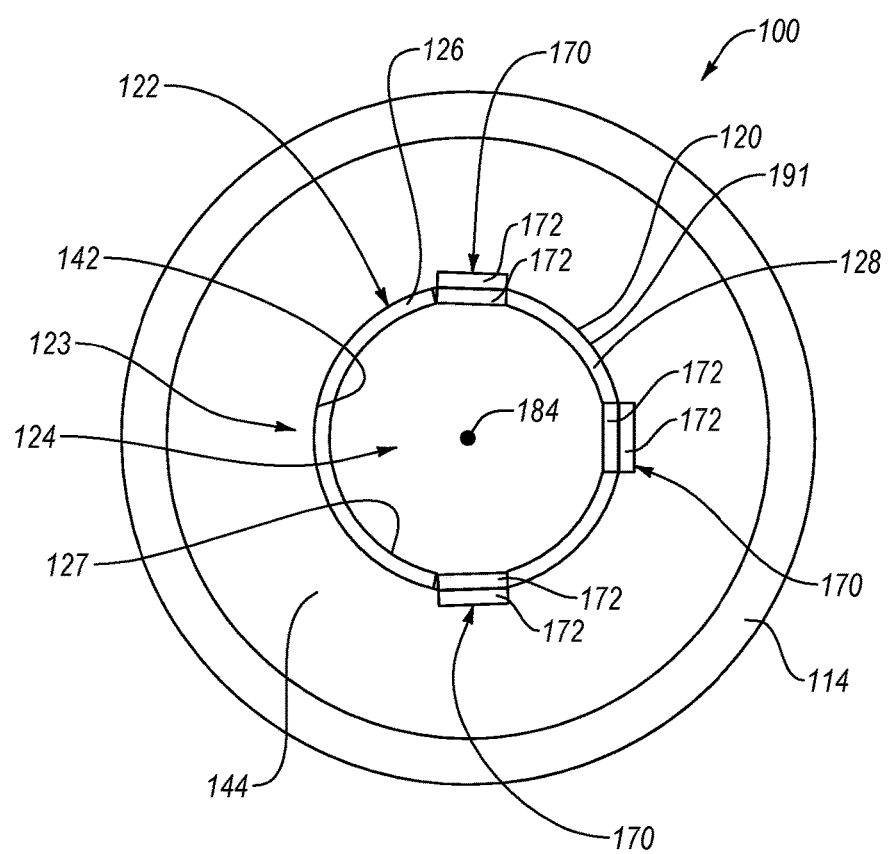
FIG. 10 is a schematic bottom plan view of a probe, according to one or more examples of the present disclosure.

The sensor assemblies 170 are held in place within the interior channel 118 by the insulation ring 140. More specifically, the sensor assemblies 170 are coupled to the insulation ring 140. According to one implementation, the sensor assemblies 170 are at least partially embedded in the insulation ring 140. Referring to FIGS. 9 and 10, the insulation ring 140 suspends the sensor assemblies 170 in a location offset (e.g., radially outward) from the central axis 184 of the probe 100. According to FIG. 9, in an implementation, the sensor assemblies 170 are coupled to an interior surface 142 of the insulation ring 140 and protrude radially inward from the interior surface 142 into the second interior channel 124 defined by the inner shield 120. In contrast, in FIG. 10, at least one sensor 172 of each sensor assembly 170 is embedded within the insulation ring 140 such that the sensor assemblies 170 do not protrude into the second interior channel 124.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The present subject matter may be embodied in other specific forms without departing from its spirit or essential characteristics. The described embodiments are to be considered in all respects only as illustrative and not restrictive. All changes which come within the meaning and range of equivalency of the claims are to be embraced within their scope.

What is claimed is:

1. A probe for detecting structural integrity of a part, the probe comprising:
    an outer shield, having a hollow tubular shape, defining a first interior channel, and comprising a part-engagement end;
    an inner shield, within the first interior channel, having a hollow tubular shape, spaced apart from the outer shield, and comprising a first end portion and a second end portion, opposite the first end portion, wherein:
        the first end portion of the inner shield is closer to the part-engagement end of the outer shield than the second end portion of the inner shield; and
        the first end portion of the inner shield comprises a wall extension, protruding in a direction extending from the second end portion of the inner shield to the first end portion of the inner shield and circumferentially extending about less than an entire circumference of the inner shield; and
    an induction coil, within the first interior channel of the outer shield between the outer shield and the inner shield.

2. The probe according to claim 1, further comprising an insulation ring, within the first interior channel between the outer shield and the inner shield and between the induction coil and the part-engagement end of the outer shield.

3. The probe according to claim 2, wherein:
    the outer shield is made of a magnetic material;
    the inner shield is made of a magnetic material; and
    the insulation ring is made of a non-magnetic material.

4. The probe according to claim 1, wherein the wall extension circumferentially extends about less than or equal to 60% of the entire circumference of the inner shield.

5. The probe according to claim 1, further comprising a visual indicator, external to the outer shield and radially aligned with the wall extension.

6. The probe according to claim 1, wherein:
    the wall extension comprises a first distal end; and the first distal end terminates at a first plane between the part-engagement end of the outer shield and the induction coil.

7. The probe according to claim 1, wherein the first end portion of the inner shield further comprises a cut-out space contiguous with the wall extension and extending about less than the entire circumference of the inner shield.

8. The probe according to claim 7, further comprising a magnetic field sensor positioned at each of multiple locations within the cut-out space of the inner shield.

9. A probe for detecting structural integrity of a part, the probe comprising:
   an outer shield, having a hollow tubular shape, defining a first interior channel, and comprising a part-engagement end;
   an inner shield, within the first interior channel, having a hollow tubular shape, spaced apart from the outer shield, and comprising a first proximal end and a first distal end, opposite the first proximal end; and
   an induction coil, within the first interior channel of the outer shield between the outer shield and the inner shield;
   wherein:
      the first distal end of the inner shield terminates at a first plane between the part-engagement end of the outer shield and the induction coil;
      the inner shield further comprises a first end portion and a second end portion, opposite the first end portion;
      the first end portion of the inner shield comprises a wall extension, protruding in a direction extending from the second end portion of the inner shield to the first end portion of the inner shield and circumferentially extending about less than an entire circumference of the inner shield; and
      the first distal end of the inner shield is defined by the wall extension.

10. The probe according to claim 9, wherein the first distal end of the inner shield has an at least partially annular shape.

11. The probe according to claim 9, wherein:
    the first plane is a first distance away from the part-engagement end of the outer shield;
    the induction coil is a third distance away from the part-engagement end of the outer shield; and
    the first distance is at most about half of the third distance.

12. The probe according to claim 9, wherein:
    the first plane is a first distance away from the part-engagement end of the outer shield;
    the first end portion of the inner shield further comprises a cut-out space contiguous with the wall extension and extending about less than entire circumference of the inner shield;
    the first end portion of the inner shield further comprises a second distal end of the inner shield;
    the wall extension and the second distal end of the inner shield define the cut-out space;
    the second distal end of the inner shield terminates at a second plane;
    the second plane is a second distance away from the part-engagement end of the outer shield; and
    the second distance is greater than the first distance.

13. The probe according to claim 12, further comprising a magnetic field sensor positioned at each of multiple locations within the first interior channel of the outer shield, wherein each magnetic field sensor is positioned at least a fourth distance away from the part-engagement end of the outer shield and at most a fifth distance away from the part-engagement end of the outer shield.

14. A probe for detecting structural integrity of a part, the probe comprising:
    an outer shield, having a hollow tubular shape, defining a first interior channel, and comprising a part-engagement end;
    an inner shield, within the first interior channel, having a hollow tubular shape, spaced apart from the outer shield;
    an induction coil, within the first interior channel of the outer shield between the outer shield and the inner shield; and
    at least one sensor assembly within the first interior channel of the outer shield between the part-engagement end of the outer shield and the induction coil, wherein the at least one sensor assembly comprises at least two magnetic field sensors abut each other in a side-by-side or end-to-end manner;
    wherein the first end portion of the inner shield comprises a wall extension, protruding in a direction extending from the second end portion of the inner shield to the first end portion of the inner shield and circumferentially extending about less than an entire circumference of the inner shield.

15. The probe according to claim 14, further comprising an insulation ring within the first interior channel between the outer shield and the inner shield, wherein the at least one sensor assembly is coupled directly to the insulation ring.

16. The probe according to claim 15, wherein:
    the inner shield comprises a distal end; and
    the insulation ring suspends the at least one sensor assembly in an axially spaced apart manner relative to the distal end of the inner shield and the part-engagement end of the outer shield.

17. The probe according to claim 14, wherein the at least two magnetic field sensors of the at least one sensor assembly are stacked together in a direction perpendicular to a central axis of the outer shield and the inner shield.

18. The probe according to claim 14, wherein the probe comprises multiple sensor assemblies spaced apart from each other about at least a portion of a circumference of the inner shield.

19. The probe according to claim 14, wherein:
    the inner shield comprises a first end portion and a second end portion, opposite the first end portion;
    the first end portion of the inner shield is closer to the part-engagement end of the outer shield than the second end portion of the inner shield;
    the wall extension defines a distal end of the inner shield that terminates at a first plane between the part-engagement end of the outer shield and the induction coil;
    the first end portion of the inner shield further comprises a cut-out space contiguous with the wall extension and extending about less than entire circumference of the inner shield; and
    the at least one sensor assembly is at least partially within the cut-out space of the first end portion of the inner shield.

* * * * *